United States Patent
Maier et al.

(10) Patent No.: US 7,033,837 B1
(45) Date of Patent: Apr. 25, 2006

(54) METHOD FOR COMBINATORIAL MATERIAL DEVELOPMENT USING DIFFERENTIAL THERMAL IMAGES

(75) Inventors: Wilhelm F. Maier, Essen (DE); Arnold Holzwarth, Villeurbanne (FR)

(73) Assignee: hte Aktiengesellschaft the high throughput experimentation company, Heidelberg (DE)

( * ) Notice: Subject to any disclaimer, the term of this patent is extended or adjusted under 35 U.S.C. 154(b) by 0 days.

(21) Appl. No.: 09/582,116

(22) PCT Filed: Dec. 15, 1998

(86) PCT No.: PCT/EP98/08214

§ 371 (c)(1),
(2), (4) Date: Sep. 18, 2000

(87) PCT Pub. No.: WO99/34206

PCT Pub. Date: Jul. 8, 1999

(30) Foreign Application Priority Data

Dec. 23, 1997 (DE) .......................................... 197 57 754
Jun. 12, 1998 (DE) .......................................... 198 26 303

(51) Int. Cl.
*G01N 33/00* (2006.01)
*G01N 21/29* (2006.01)
*G01N 25/20* (2006.01)
*G01N 25/22* (2006.01)
*B01J 31/00* (2006.01)

(52) U.S. Cl. .................. 436/37; 436/147; 436/149; 436/159; 435/DIG. 10; 422/82.05; 422/68.1; 502/100; 502/102; 502/114

(58) Field of Classification Search .................. 435/7.1, 435/DIG. 10, DIG. 9, DIG. 11, DIG. 13, 435/DIG. 14–19; 436/37, 147, 149, 159; 422/82.05, 68.1; 502/100, 102, 114
See application file for complete search history.

(56) References Cited

U.S. PATENT DOCUMENTS 6,063,633 A * 5/2000 Willson, III .................. 436/37

FOREIGN PATENT DOCUMENTS

| WO | WO 96 11878 A | 4/1996 |
|----|---------------|--------|
| WO | WO 97 32208 A | 9/1997 |
| WO | WO 98 03521 A | 1/1998 |

* cited by examiner

*Primary Examiner*—Padmashri Ponnaluri
(74) *Attorney, Agent, or Firm*—Jones Day

(57) ABSTRACT

A method for the combinatorial development of materials in which heat changes caused by chemical or physical processed with materials of combinatorial libraries are visualized using heat different images form an infrared camera. As said libraries, all kinds of material libraries, such as heterogeneous or homogeneous catalysts or enzymes, can be used.

18 Claims, 5 Drawing Sheets

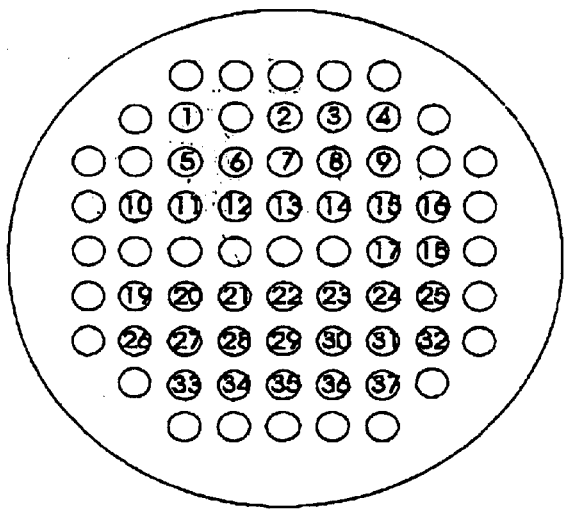

| | | | | | |
|---|---|---|---|---|---|
| 1 | Ir₁Ti | 14 | Ni₅Ti | 27 | Zn₅Si |
| 2 | Pt₁Ti | 15 | Rh₅Ti | 28 | V₅Si |
| 3 | Pt₂Ti | 16 | Ru₅Ti | 29 | Mn₃Si |
| 4 | Pt₅Ti | 17 | Cu₅Ti | 30 | Mn₅Si |
| 5 | Zn₅Ti | 18 | Cu₅Si | 31 | Fe₅Si |
| 6 | V₅Ti | 19 | Pd₁Si | 32 | Fe₁₀Si |
| 7 | Mn₃Ti | 20 | Pd₅Si | 33 | Ir₂Si |
| 8 | Mn₅Ti | 21 | Cr₅Si | 34 | Ir₅Si |
| 9 | Fe₅Ti | 22 | Co₅Si | 35 | Pt₁Si |
| 10 | Pd₁Ti | 23 | Ni₅Si | 36 | Pt₂Si |
| 11 | Pd₅Ti | 24 | Rh₅Si | 37 | Pt₅Si |
| 12 | Cr₅Ti | 25 | Ru₅Si | | |
| 13 | Co₅Ti | 26 | Ti₅Si | | |

Figure 1 Design of the catalyst library of example 1: f.e. Co₅Si stands for 5 mol% colbat oxide in 95 mol % SiO₂, Co₅Ti stands for 5 mol% cobalt oxide in 95 mol % TiO₂

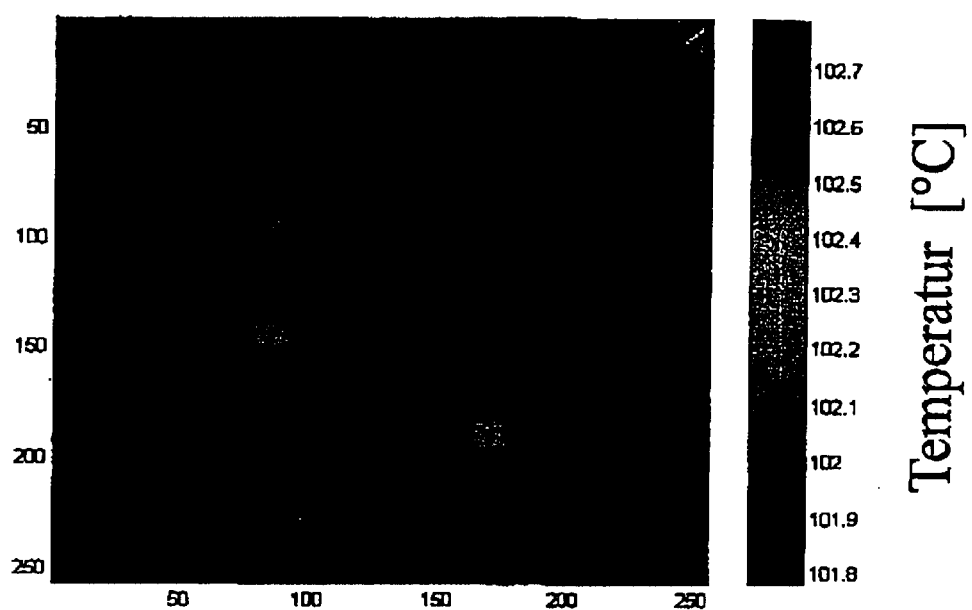
Figure 2  IR-image with temperature scale (right) during hydrogenation of 1-hexine at 100 °C

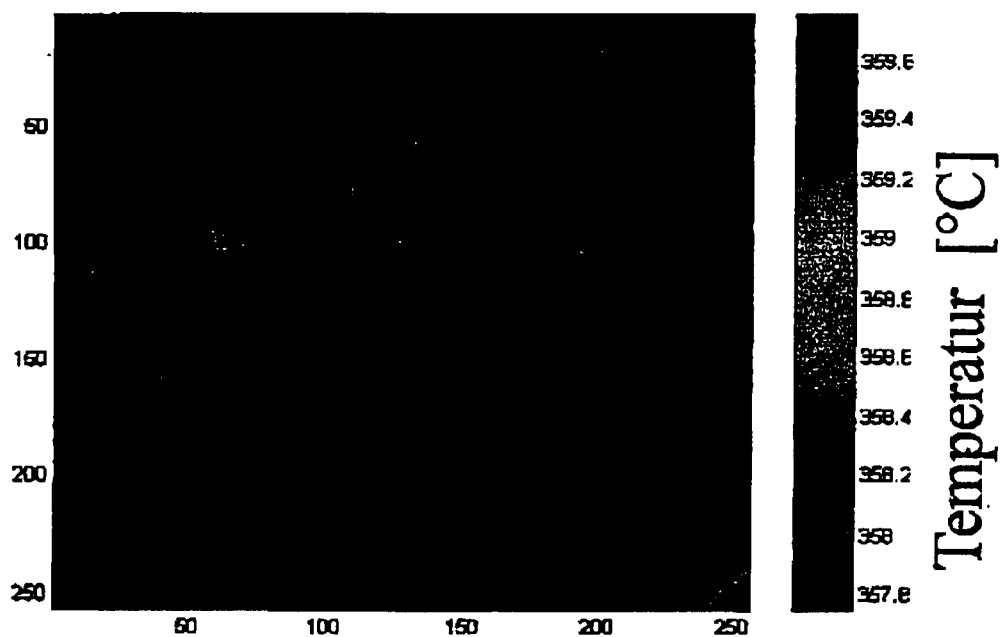
Figure 3   IR-image with temperature scale (right) during oxidation of isooctane with synthetic air 350 °C
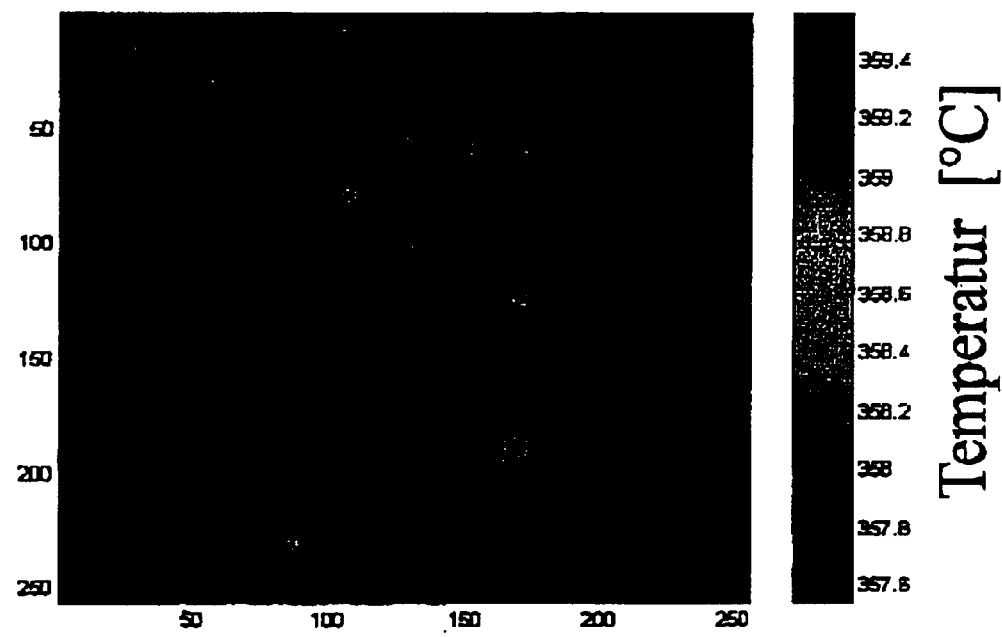
Figure 4   IR-image with temperature scale (right) during oxidation of toluene with synthetic air 350 °C

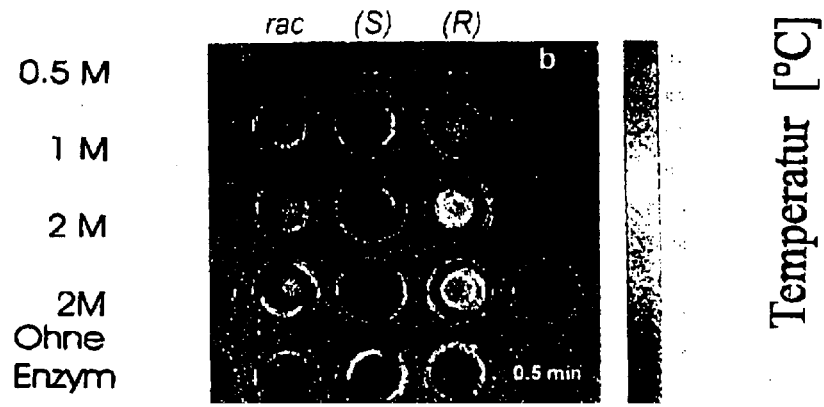
Figure 5 IR-image with temperature scale (right) during the lipase catalysed enantioselective acylation of 1-phenylethanol with vinylacetate at 30 °C
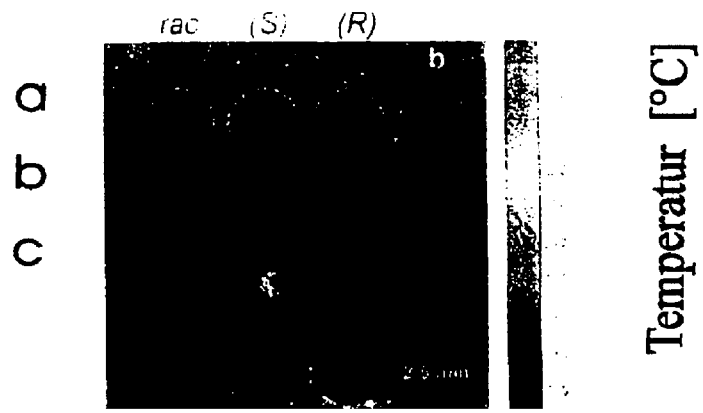
Figure 6 IR-image with temperature scale (right) during the enantioselective hydrolysis of epichlorohydrine with various metal-Salen catalysts at 27 °C

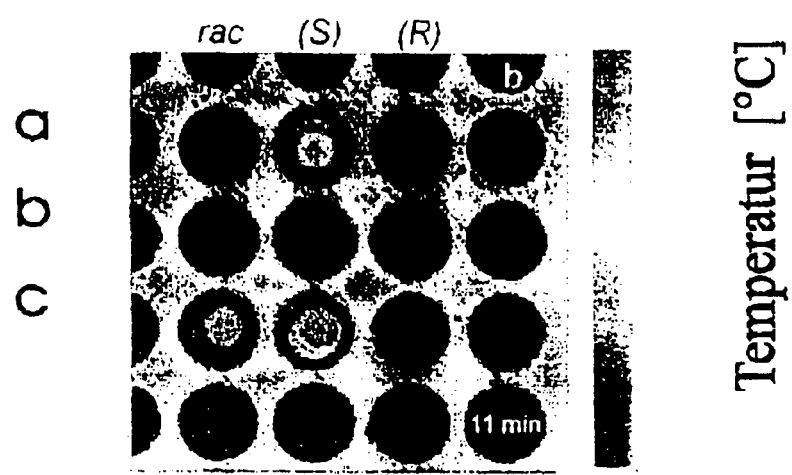
Figure 7  IR-image with temperature scale (right) during the enantioselective hydrolysis of various substrates with a cobalt-Salen catalyst at 27 °C

METHOD FOR COMBINATORIAL MATERIAL DEVELOPMENT USING DIFFERENTIAL THERMAL IMAGES

This application is a 371 of PCT/EP98/08214 filed on Dec. 15, 1998.

The present invention relates to a method for the comparative determination of properties of the materials of a combinatorial library using an infrared camera which records the heat changes of chemical or physical processes in the form of a difference image. The essential features of the invention have already been described in the application DE 197 57 754.7 of Dec. 23, 1997. The present application contains an extension of the method by the use of selective IR filters, its use for the general characterization of material properties, its use for homogeneous catalysts, and an improved embodiment with library plates of low IR reflectivity, such as slabs of state.

PRIOR ART

The narrowest bottleneck in the development of new materials is the discovery of suitable new leading structures. In particular, this applies to new catalysts. Despite the wide-spread use of heterogeneous and homogeneous catalysts in chemical technology and the related extensive research efforts, the detailed mechanism of action of heterogeneous and homogeneous catalysts under industrial reaction conditions is not sufficiently known. Therefore, one has to rely on empirical methods for selecting appropriate catalyst materials for each application and finding reaction conditions under which a desired catalytic activity and selectivity occurs. Classical test methods for catalysts require that each candidate catalyst material is Individually tested under the reaction conditions, which is a very expensive and also time-consuming procedure in view of the immeasurable abundance of possible materials. A promising solution is offered in the field of combinatorial materials sciences for making a reasonable preselection of heterogeneous and homogeneous catalyst materials for technically interesting reactions and limiting the test method to a few promising materials. While heterogeneous catalysts are predominantly important to the production of mass products and fine chemicals, homogeneous catalysts are dominating in the production of optically pure active substances in the pharmaceutical field and in tactility-controlled polymerization.

In the so-called combinatorial methods, a large number of samples is applied to a support within a very small space. Then, using readily available physical measuring quantities associated with the desired property of the material, a fast and reliable is performed for this desired property on every sample.

In this way, new magnetoresistant materials [B. Gabriel, H. Chang, X. Sun, P. G. Schultz, X.-D. Xiang, "A Class of Cobalt Oxide Magnetoresistance Materials Discovered with Combinatorial Synthesis", Science, 270, 273–275, 1995], new superconducting materials [X.-D. Xiang, X. Sun, G. Briceno, Y. Lou, K.-A. Wang, H. Chang, W. G. Wallace-Freedman, S.-W. Chen, P. G. Schultz, "A Combinatorial Approach to Materials Discovery", Science, 268, 1738–1740, 1995] and new luminescent materials [X.-D. Sun, K.-A. Wang, Y. Yoo, W. G. Wallace-Freedman, C. Gao, X.-D. Xiang, P. G. Schultz, "Solution-Phase Synthesis of Luminescent Materials Libraries", Adv. Mater. 9, 1046–1049, 1997] have already been discovered.

Even in the field of combinatorial chemistry of heterogeneous catalysts, corresponding publications already exist [F. C. Moates, M. Somani, a. Annamalai, J. T. Richardson, D. Luss, R. C. Willson, "Infrared Thermographic Screening of Combinatorial Libraries of Heterogeneous Catlysts", Ind. Eng. Chem. Res, 35, 4801–4803, 1996; R. C. Willson, "Catalyst Testing Process and Apparatus", U.S. Patent; PCT/US 97/02756, International Patent: WO 97/32208]. The authors describe an experiment in which catalytlc actvity is detected from the accompanying heat of reaction using an infrared camera. However, the detection sensitivity of the configuration described by the authors was relatively low so that only the extremely exothermic hydrogenygen reaction (14 k/g) was detected. This is not a reaction of technical importance. To effectively examine catalysts for technically important reactions, above all, a higher detection sensitivity of the measuring configuration is necessary, and evidence must be provided, that heats of reaction can be registered at low temperature with different reactions and with minute amounts of catalyst. The recognition of the catalytic activity of polymer-bound catalysts in solution was demonstrated on coded beads (0.5 mm) [S. J. Taylor, J. P. Morken, Science 280 (1998) 268]. The density of the solution must be higher than the density of the beads because the latter can only be observed when afloat on the surface. Drawbacks are the expensive coding technique and the necessity of using a solvent of higher density than that of the floating fixed-bed catalysts. In addition, there is a problem in using uncorrected infrared images, i.e., the fact that due to different emission properties, highly sensitive infrared cameras indicate the presence of different materials on a surface when no reactions take place so the practical utility of such methods is highly limited.

The reliable preparation of catalyst libraries is another important aspect. Well known are combinatorial libraries, although largely rest to the field of pharmaceutical applications, the generation of which can partly be transferred to the preparation of libraries for developing new materials as well (B. Posner et al., Trends in Biochemical Science 19 (1994) 145). One method which is probably the most reliable and most widely applicable one for the preparation of combinatorial libraries of materials is the combination of ink-jet printing technology with computer control which allows to produce the new materials dot by dot by mixing solutions in the nanoliter range and to convert them to the solids to be examined by a well-defined posttreatment [X.-D. Sun, K.-A. Wang, Y. Yoo, W. G. Wallace-Freedman, C. Gao, X.-D. Xiang, P. G. Schuit, "Solution-Phase Synthesis of Luminescent Materials libraries", Adv. Mater. 9, 1046–1049, 1997]. However, the problem here is the use of suitable synthetic conditions which allow the production of defined catalyst and other materials from the mixing of nanoliter solutions.

DESCRIPTION OF THE INVENTION

We have now found that minute heat changes occurring in the course of chemical or physical process can be reliably visualized with an infrared camera with spatial resolution when a difference heat image is recorded which results from the subtraction of the infrared emission intensities recorded prior to the beginning of the reaction from the intensities obtained under reaction conditions. Suitable chemical or physical processes with heat changes include chemical reactions, phase transitions, conversions, absorption processes (physisorption, chemisorption, adsorption, desorption), absorption processes (absorption of molecules or electromagnetic radiation), magnetic induction. Thus, the heat changes of the physisorption of molecules from the gasphase can be utilized for recognizing porosities in materials. The heat of catalyzed reactions serves for recognizing the catalytic activity of materials. The heat changes of phase transitions serve for recognizing changes in substances. The heat changes associated with surface reactions, such as the formation of carbides or nitrites by reactions of alloys or mixed oxides with methane or ammonia serve for recognizing conversions. The heat changes associated with chemisorption serves for recognizing surface reactivity, such as acidic or basic sites. The heat changes associated with the absorption of electrmagnetic radiation characterize particular absorption properties, such as ultraviolet absorption, X-ray absorption, or absorption of visible light. Magnetic properties are recognized by the heating brought about by applying a magnetic field. All these properties are of particular interest when specific materials are significantly different from the bulk of other materials and thus represent potential novel lead structures.

In particular, the method of interest for the development of new catalysts by the use of combinatorial libraries. Surprisingly, a suitable method for the preparation of combinatorial catalyst libraries with heterogeneous catalysts is the sol-gel method, as partially described in DE-A-195.450426. In addition, we have found that the heat of homoge neously catalyzed reactions can also be reliably visualized with this technique. The use of heat difference images also allows for a temperature calibration and thus a reliable assignment of the actual temperature increase at the active catalyst. This is of great importance to the evaluation of relative aches and quantifications of the catalyst performances.

The catalyst reactions are preferably conducted under exactly controlled conditions in a hermetically sealed reactor provided with an infrared-transparent window to enable recording with a camera.

Catalyst libraries consisting of catalyst components in the form of metal oxides and/or mixed metal oxides are prepared by first distributing the precursors of the catalyst components to be examined as an aqueous or alcoholic solution of silicon or metal compounds in the form of their alkoxy derivatives, mixed alkoxy derivatives, alkoxyoxo or acetylacetonate derivatives or in the form of their halides, nitrates, citrates or other carboxylates over the surface of a plate consisting of, for example, slate, metal or steel, glass, ceramic or plastic, e.g., in recesses formed by drilling into the plate. In particular, the catalyst component can be carbides, nitrites and zeoles. The library plates are subsequently dried and calcined. When the catalyst library is prepared, it may happen, due to the surface properties of the library plate, that the sol creeps out of the bores onto the surface of the library plate. This can be prevented by coating the library plate with a non-wetting infrared-transparent film in the regions not occupied by catalysts, for example, if the coating is applied before making the bores.

Not only solids, but also molecules in gases emit infrared radiation. The intensity of this thermal emission increases with temperature. Especially by reflections of this emitted radiation at reactor walls and at the surface of the catalyst library, the false impression of inhomogeneous increases of temperature can be evoked. Reflections at the catalyst library are particularly inconvenient because they are directly recorded by the infrared camera. For this reason, the radiation properties of the support material of the catalyst library are of critical importance. Therefore, a material having a particularly low reflectivity, dose to that of a black body is particularly suitable as a support material for the catalyst library. This effect may also be achieved by a suitable coating. The interior walls of the reactor should also reflect as little infrared radiation as possible. This can be achieved, for example, by appropriate antireflection coatings. In addition, the support material for the catalyst library should have as low as possible a thermal conductivity in order that heat developed at the catalyst sites during the catalytic reaction is not dissipated too fast and an increase in temperature as high as possible can be achieved.

Wavelength ranges in which the gaseous reactants and products display a particularly high infrared activity are unfavorable for IR-thermographic temperature measurements since interfering effects from the absorption and emission by the gases are more prevailing in this case. Such wavelength ranges can be reduced using a wavelength-specific infrared filter. For gaseous hydrocarbons, we have found it convenient to reduce the particularly intensive CH vibrations with such a filter.

IR thermography as described above is also suitable for recognizing the catalytic activity of enantioselectve homogeneous catalysts and enzymes. By using optically pure reactants or racemates, both the relative catalytic activities of different catalysts and their enantioselectivity can be recognized by IR thermography. Reactions examined include the enantioselective acylation of 1-phenylethanol with lipase [M. T. Reetz, A. Zonta, J. Simpelkamp, Angew. Chem. 107 (1995) 373–376] and the hydrolysis of chiral epoxides with Mn, Co and Cr salene complexes [M. Tokunaga, J. F. Larrow, F. Kakiuchi, E. N. Jacobsen, Science 277 (1997) 936–9389] in a small combinatorial library of 9 reaction solutions. Using the IR-thermographic difference images, both the relative activities of the catalysts and their enantioselectivity could be simultaneously visalized.

The method can of course be applied to many other types of reactions, such as selective hydrogenations, selective oxddations, esterifications, pericydic reactions, halogenations, dehalogenations, hydrogenolyees, hydrations, dehydrations, condensations, enantioselective reactions, polymerization reactions, polycondensation reactions, oxidative couplings, and selective oxidations of olefins and alkanes, especially with air, $H_2O_2$ or ozone with the selective formation of epoxides, ketones, aldehydes, alcohols, carboxylic acids or anhydrides. Heats of such reactions in liquid phase can also be visualized very simply and effectively using an infrared camera (Maier, Holzwarth, DE 19757 754.7).

EXAMPLES

Construction of the Camera, Correction of the Detector and Temperature Calibration:

In the following Examples, an AIM AEGAIS infrared camera was employed with a PtSi (platinum/silicon) detector with 256 times 256 pixels as described in the following. The camera was connected with a computer. The software (version 1.40 of Jul. 4, 1997) allowed to subtract the background in such a way that only an increase in temperature relative to the starting temperature is indicated in each pixel.

Directly before the entrance window of the detector, a 3.6 μm infrared cut-off filter was applied which is opaque to infrared radiation having wavelengths of shorter than 3.6 μm. The inhomogenity of the detector was corrected for by a two-point correction. Thus, IR images of the library were recorded 5° C. below and above the reaction temperature (hydrogenation: 100° C.; oxidation: 350° C.; lipase catalysis: 30° C.; meal salene catalysis: 27° C.). After reaching the reaction temperature prior to the start of the reaction, another infrared image of the catalyst library was recorded. This image was then subtracted from all following infrared images (offset) so that only temperature changes due to catalytic activity at the catalyst sites became visible through corresponding color changes. The temperature calibration was effected by recording in the catalyst library in the reactor at 6 temperatures, followed by fitting the individual pixels using a quadratic polynomial, a function provided for in the camera software.

Example 1

Combinatorial Test Method for Screening the Catalytic Activity of Materials From a Library Construction of the Reactor When the reactor was constructed, particular care was taken that a temperature distribution as homogeneous as possible within the reactor was achieved. The reactor essentially consists of two portions, the reactor head with an infrared-transparent barium fluoride window for observing the catalyst library, and the reactor block, which consists of solid steel. The reactor head with the infrared-transparent barium fluoride window forms an angle of 10°. The heating elements are in the lower portion of the reactor. They are arranged in such a way that the complete reactor block and reactor head are heated up as homogeneously as possible. The gas inlets were led from below through the reactor block into the reaction chamber with the catalyst library in order to preheat the gaseous educts to the same temperature as prevails at the catalyst library prior to the reaction at the catalyst sits. The gas mixture was fed through a multitude of small holes arranged around the circular catalyst library in order to achieve as homogeneous as possible a distribution of the gases in the chamber.

Preparation of the Silica Sols:

Silica and titania sols were prepared and pipetted into appropriate bores on a slate library plate using a microliter pipette. After the solvent was evaporated, the whole library was calcined. The plate was inserted into a special reactor, designed for observation with the infrared camera (see above). Then, the catalysts on the plate were activated by tempering at 300° C. in a hydrogen flow for tree hours. Then, experiments for the hydrogenation of 1-hexane were performed at 100° C. Finally, the experiments on the oxidation of isooctane and toluene with synthetic air were performed at 350° C. Silica sols were prepared by the standard protocol of klein et al. [S. Klein, S. Thorimbert, W. F. Maier, J. Catal. 163 (1996) 476–488]. Tetraethoxy orthosilicate served as a silica precursor. The following compounds were dissolved in the sol as precursors of the other elements: $PdCl_2$, $Na_2PtCl_6$, $Ira_4 \cdot H_2O$, $RuCl_3H_2O$, $COCl_2 \cdot 6H_2O$, $Fe(acac)_3$, $Mn(acac)_3$, $(iPrO)_3VO$, $CrCl_3 \cdot 6H_2O$, $Cu(acac)_2$, $Ni(acac)_2$, $ZnCl_2$, $Pd(acac)_2$, $RhCl_3 \cdot 3H_2O$.

Preparation of the Titania Sols:

With constant stirring, 1 ml of titanium isopropoxide (3.36 mmol) was dissolved in 3.33 ml of dry ethanol. After 30 minutes of stirring, 8.33 ml of 8 N HCl was added. After another 5 minutes, 46.7 ml of 12 N HCl was slowly added in the course of 20 min. Then 833 ml of ethanol was added. Finally, 833 ml of an ethanolic solution of the metal compound was added.

Preparation of the Catalyst Library:

As the material for the catalyst library, slate was selected due to its low thermal conductivity and its low reflectivity for infrared radiation. The circular library plate (diameter 5 cm) had 69 holes with diameters of 1.5 mm and a depth of 0.6 mm.

The catalyst library was prepared by pipetting microliter amounts of the silica and titania sols into the designated bores on the slate plate. In order to obtain comparable amounts of catalyst material, 1.5 μl was pipetted in the case of the silica sols (corresponding to 192 μg of silica), and 5 μl was pipetted in the case of the titania sols (corresponding to 182 μg of titania). After evaporating the solvent, the plate was calcined as in Example 1 (temperature program: (1) from room temperature to 65° C. at 1° C./min, (2) maintain temperature at 65° C. for 30 min, (3) from 65° C. to 250° C. at 1° C./min, (4) maintain temperature at 250° C. for 3 h, (5) cool down to room temperature). FIG. 1 shows the design and chemical compositions of the library.

Hydrogenation of 1-hexyne:

The hydrogenation of 1-hexyne was performed by passing hydrogen at a temperature of 100° C. through the reactor at a flow rate of 20 ml/min. 1-Hexyne was evaporated into the gas flow. The concentration of 1-hexyne in the gas phase was 0.2478 g/l.

FIG. 2 shows an infrared image of the catalyst library during the reaction, the allocation of the library can be seen in FIG. 1. A particularly high activity is exhibited by catalyst materials $Pd_5Si$, $Pd_1Si$, $Pt_5Si$ and $Pt_1Si$.

Oxidation of Isooctane With Synthetic Air:

The oxidation of isoocane was performed by passing synthetic air at a temperature of 350° C. through the reactor at a flow rate of 20 ml/min. Isooctane was evaporated into the gas flow. The concentration of isooctane in the gas phase was 0.2381 g/l. FIG. 3 shows an infrared image of the catalyst library during the reaction. A particularly high activity is exhibited by catalyst materials $Pt_2Ti$, $Pt_1Ti$, $V_5Ti$, $Pd_1Ti$, $Ru_5Ti$, $Cu_5Ti$.

Oxidation of Toluene With Synthetic Air:

The oxidation of toluene was performed by passing synthetic air at a temperature of 350° C. through the reactor at a flow rate of 20 ml/min. Toluene was evaporated into the gas flow. The concentration of toluene in the gas phase was 0.1489 g/l. FIG. 4 shows an infrared image of the catalyst library during the reaction. A particularly high actvity is exhibited by catalyst materials $Pt_2Ti$, $Pt_1Ti$, $V_5T_i$, $Cu_5Ti$, $Pt_5Ti$, $Pt_5Si$.

Example 2

Combinatorial Test Method for the Simultaneous Screening for Activity and Enantioselectivity of Homogeneous Catalyst Catalytic reactions in the liquid phase were performed in the wells of a modified microtitration plate. This plate was attached onto a thermally controlled Eppendorf shaker. By quickly shaking the microtitrution plate, it was possible to achieve homogeneous mixing of the reaction solutions within the individual wells of the plate and to control the temperature of the solutions to particular predetermined temperatures. The adjustment of the infrared camera was done as described in the previous Example. Constant shaking was applied during the reaction. For measuring with the infrared camera, the shaker was briefly stopped. In this experiment, a library of 9 reactions were observed simultaneously.

Lipase-catalyzed Enantioselective Acylation of 1-Phenylethanol With Vinyl Acetate 100 μl each of a solution of the phenylethanol as an S enantiomer, R enantiomer or racemate in toluene was pipetted into the wells of the microtitration plate. To these solutions was added 100 μl of a solution of vinyl acetate in toluene in an equimolar ratio. Concentrations of 0.5 M, 1 M or 2 M were respectively used. Then, infrared images of the plate with the solutions for temperature calibration, two-point correction of the detector and offset were recorded. Subsequently, the reaction was started by adding 5 mg of Immobilized lipase (*Candida antarctica*, Novo SP 435) at 30° C., and infrared images of the plate with the solutions were recorded at different times during the reaction, FIG. 5 shows that the heat evolution is lower for the racemate (left column) than for the R enantiomer of 1-phenylethanol (right column) whereas the S enantiomer (middle column) is not converted by the enzyme.

Enantioselective Hydrolysis of Epiclorohydrn With Manganse-, Chmomium- and Cobalt-salene Catalysts Three times 300 µl each of a solution respectively containing 600 µmol of the catalysts (S,S)-M-salene (a: M=Mn; b: M=Cr; c: M=Co) in toluene was pipetted into the wells of the microtitration plate. Then, 78.4 µl (1 mmol) of the eplehlorohydrin was added as a racemate, S or R enantiomer. Then, infrared images of the plate with the solutions were recorded for temperature calibration, two-point correction of the deter and offset. Subsequently, the reaction was started by adding 9.9 µl (0.55 mmol) of water at 27° C., and images of the plate with the solutions were recorded at different times during the reaction. FIG. 6 shows that the manganese catalyst (a) is not active, the chromium catalyst (b) shows a detectable reaction only with the S-epichlorohydrin, while the cobalt catalyst (c) is the most active, the S enantiomer reacting better than the racemate. None of the catalysts shows a detectable reaction with the R enantiomer.

Hydrolysis of Different Substrates With a Cobalt-salene Catalyst:

Into 9 wells of the microtitration plate was pipetted 100 µl each of a solution containing 2 µmol of the catalyst (S,S)-Co-salene in toluene. Then, solutions of epoxides d–f were added as a racemate, S or R enantiomer (d–f=epoxides of formulae $RCHCH_2O$: d: $R=CH_2OCH_2Ph$; e: $R=Ph$; f: $R=CH_2Cl$). The solutions contained the epoxides in a concentration of 3.85 mol/l. Prior to starting the reaction by the addition of water at 27° C., infrared images of the plate with the solutions were again recorded for temperature calibration, two-point correction of the detector and offset. After the addition of water, infrared images of the plate with the solutions were recorded at different times during the reaction. FIG. 7 shows that the Co catalyst selectively reacts with the S enantiomers of epoxides a and b.

What is claimed is:

1. A method for determining heat changes in chemical compounds caused by catalytic activity, the method comprising:

initiating physical or chemical processes by exposing chemical compounds to catalysts that are arranged in the form of a catalytic library over the surface of a library plate; and recording a difference image of the heat changes in the chemical compounds using an infrared camera;

wherein the image is obtained by subtracting an infrared emission recorded prior to the beginning of the processes from an infrared emission recorded during the course of the processes and wherein said library plate consists of slate.

2. A method according to claim 1, wherein the library plate is coated with a non-wetting infrared-transparent film in the regions not occupied by catalyst.

3. A method according to claim 1, wherein the library plate comprises anti-reflection coatings.

4. A method according to claim 1, wherein a wavelength specific infrared filter is used.

5. A method according to claim 1, wherein an infrared transparent window is situated between the infrared camera and the catalysts.

6. A method according to claim 1, wherein the catalyst components are carbides, nitrides or zeolites.

7. A method according to claim 1, wherein the library plate contains reaction cavities comprising liquid reaction solutions with homogeneous catalysts.

8. A method according to claim 7, wherein enzymes or soluble organometallic compounds are employed as said catalysts.

9. A method according to claim 1 or 7 wherein the selectivity or the enantioselectivity of catalyzed reactions is determined on the library.

10. A method for determining heat changes in chemical compounds caused by catalytic activity, the method comprising:

initiating physical or chemical processes by exposing chemical compounds to catalysts that are arranged in the form of a catalytic library over the surface of a library plate; and detecting heat changes in the chemical compounds with an infrared camera with spatial resolution;

wherein a difference image of the heat changes is recorded, the difference image resulting from the subtraction of the infrared emission intensities recorded prior to the beginning of the reaction from the intensities obtained under reaction conditions, and the library plate has an IR-reflectivity close to, at or below the IR-reflectivity of slate.

11. A method according, to claim 10, wherein the library plate is coated with a non-wetting infrared-transparent film in the regions not occupied by catalyst.

12. A method according to claim 10, wherein the library plate comprises anti-reflection coatings.

13. A method according to claim 10, wherein a wavelength specific infrared filter is used.

14. A method according to claim 10, wherein an infrared transparent window is situated between the infrared camera and the catalysts.

15. A method according to claim 10, wherein the catalyst components are carbides, nitrides or zeolites.

16. A method according to claim 10, wherein the library plate contains reaction cavities comprising liquid reaction solutions with homogeneous catalysts.

17. A method according to claim 16, wherein enzymes or soluble organometallic compounds are employed as said catalysts.

18. A method according to claim 10 or 16, wherein the selectivity or the enantioselectivity of catalyzed reaction is determined on the library.

* * * * *